United States Patent
Kruse et al.

(10) Patent No.: US 8,402,813 B2
(45) Date of Patent: Mar. 26, 2013

(54) SENSOR ELEMENT OF A GAS SENSOR

(75) Inventors: Peer Kruse, Bietigheim-Bissingen (DE); Enno Baars, Leonberg (DE); Alexander Hetznecker, Ettlingen (DE); Lothar Diehl, Gerlingen (DE); Henrik Schittenhelm, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 115 days.

(21) Appl. No.: 12/530,395

(22) PCT Filed: Feb. 12, 2008

(86) PCT No.: PCT/EP2008/051682
§ 371 (c)(1),
(2), (4) Date: Mar. 11, 2010

(87) PCT Pub. No.: WO2008/113644
PCT Pub. Date: Sep. 25, 2008

(65) Prior Publication Data
US 2010/0180668 A1 Jul. 22, 2010

(30) Foreign Application Priority Data
Mar. 21, 2007 (DE) .................. 10 2007 013 522

(51) Int. Cl.
*G01N 7/00* (2006.01)
(52) U.S. Cl. .................................... 73/23.33
(58) Field of Classification Search .......... None
See application file for complete search history.

(56) References Cited

U.S. PATENT DOCUMENTS

| | | | |
|---|---|---|---|
| 4,636,767 A | 1/1987 | Barger et al. | |
| 5,698,089 A | 12/1997 | Lewis et al. | |
| 6,280,586 B1 | 8/2001 | Wolf et al. | |
| 6,813,931 B2 * | 11/2004 | Yadav et al. | 73/31.05 |
| 6,959,618 B1 * | 11/2005 | Larsen | 73/865.5 |
| 7,088,567 B2 * | 8/2006 | Hunt et al. | 361/277 |
| 7,347,974 B1 * | 3/2008 | Snow et al. | 422/90 |
| 7,523,006 B2 | 4/2009 | Muhl et al. | |
| 2003/0057968 A1 | 3/2003 | Wang et al. | |
| 2004/0063152 A1 | 4/2004 | Gumbrecht et al. | |
| 2007/0264158 A1 | 11/2007 | Schmidt et al. | |
| 2008/0036444 A1 | 2/2008 | Paulus et al. | |
| 2008/0150556 A1 | 6/2008 | Han et al. | |
| 2008/0264146 A1 | 10/2008 | Roesch et al. | |
| 2009/0126458 A1 | 5/2009 | Fleischer et al. | |

FOREIGN PATENT DOCUMENTS

| | | |
|---|---|---|
| DE | 19512117 | 10/1996 |
| DE | 197 51 128 | 5/1999 |
| DE | 10058397 | 6/2002 |
| DE | 10202002 | 8/2003 |

(Continued)

OTHER PUBLICATIONS

International Search Report, PCT International Patent Applicaiton No. PCT/EP2008/051682, dated Jan. 23, 2009.

*Primary Examiner* — Robert R Raevis
(74) *Attorney, Agent, or Firm* — Kenyon & Kenyon LLP

(57) ABSTRACT

A sensor element for determining a gas component or particles in a measuring gas, having a first and a second measuring electrode, the measuring electrodes being developed as interdigital electrodes having a row of intermeshing branches as well as a main conductor each, to which the branches are connected in an electrically conducting manner; and the branches of the interdigital electrodes being aligned essentially in parallel to a longitudinal axis of the sensor element.

13 Claims, 2 Drawing Sheets

FOREIGN PATENT DOCUMENTS

| | | |
|---|---|---|
| DE | 102004045210 | 4/2006 |
| DE | 102004046882 | 4/2006 |
| DE | 102005030134 | 1/2007 |
| JP | 2000 286216 | 10/2000 |
| WO | WO 2005/124326 | 12/2005 |
| WO | WO 2006/077197 | 7/2006 |
| WO | WO 2007/000368 | 1/2007 |

* cited by examiner

SENSOR ELEMENT OF A GAS SENSOR

FIELD OF THE INVENTION

The present invention relates to a sensor element for determining a gas component or particles in a measuring gas, as well as a method for its production and its use.

BACKGROUND INFORMATION

The effective use of exhaust gas aftertreatment systems assumes their control with respect to their reliability in continuous operation. For this, sensors are required using which, even in long term operation, it is possible, for instance, to ascertain exactly the particle concentration currently present in a combustion exhaust gas. In addition, the use of such sensors should enable a loading prognosis of, for instance, a Diesel particulate filter provided in an exhaust gas system, in order to attain a high degree of system safety and thereby allow the use of more cost-effective filter materials. Resistive soot sensors are particularly suitable for this application, and they draw upon the change in resistance of an interdigital electrode structure, based on the adsorption of soot for the detection of the soot.

A sensor for detecting soot in a fluid flow is described in German Patent Application No. DE 10 2004 046 882 A1, which is developed on the basis of a ceramic substrate. It includes two measuring electrodes, set apart from each other, which are developed as interdigital electrodes, that are exposed to the combustion exhaust gas that is to be tested. If soot deposits between the measuring electrodes, this results in a reduction of the insulation resistance of the ceramic material. This is detected, and a soot concentration in the fluid flow is assigned. A heating element of the sensor makes it possible to rid the electrodes and their surroundings of adsorbed soot particles via a thermal process.

The production of such resistive ceramic particle sensors first takes place on a common ceramic substrate. Finally, a separation of the corresponding sensor elements takes place. Conditioned upon the production tolerances, for instance, when the measuring electrodes of the sensor element are applied using screen printing, they are applied only in a limited area of the sensor surface, so as to avoid that, when the sensor elements are separated, the printed circuit traces of the electrodes are severed and the sensor becomes inoperable. Based on these tolerances, and depending on the positioning within the tolerance range, the electrodes are situated more or less centered on the sensor element. It has turned out, however, that the sensor functionality of a sensor element shows a clear dependence on the positioning of the electrode on the sensor element. Therefore, the production tolerances lead to a specimen variance in the resulting sensor elements, when the sensor elements are separated.

SUMMARY

It is an object of the present invention to provide a sensor element, for sensors for determining a gas component or particles in a measuring gas, and a method for its production, whose sensor functionality is generally independent of production tolerances during the separation of the sensor elements.

This object may be attained by a sensor element and by a method according to example embodiments of the present invention.

This is based particularly on the measuring electrodes of the sensor element being positioned on a surface of the sensor element in such a way that, during the separation process of the sensor elements, they are able to separated in a specified manner, without being impaired in their functioning. For this reason, it is possible deliberately to position the measuring electrodes of the sensor element all the way at the outer edge of the sensor element. In this way, for one thing, a manufacturing tolerance caused by the separation process is avoided, and secondly, the sensor sensitivity rises disproportionally, since an enlargement of the sensitive are is achieved, and in addition, the sensitivity of electrodes in the vicinity of the outer edge of a sensor element is especially pronounced, based on the favorable inflow conditions for an entering measuring gas.

It may be advantageous if the measuring electrodes are developed as interdigital electrodes, whose branches are at a distance of 40 to 200 μm apart. In this way, it is reliably ensured that even slight particle concentrations may be detected in a foreseeable time period.

Furthermore, it may be of advantage if the sensor element has a heating element or a temperature sensor. This makes a temporary heating and regeneration of the sensor element possible, as well as a temperature compensation for the measuring signals ascertained using the sensor element.

The example sensor element may be used advantageously for determining soot in exhaust gases of internal combustion engines or of stationary combustion systems.

BRIEF DESCRIPTION OF THE DRAWINGS

The present invention is explained in greater detail below.

DETAILED DESCRIPTION OF EXAMPLE EMBODIMENTS

Figure 1:
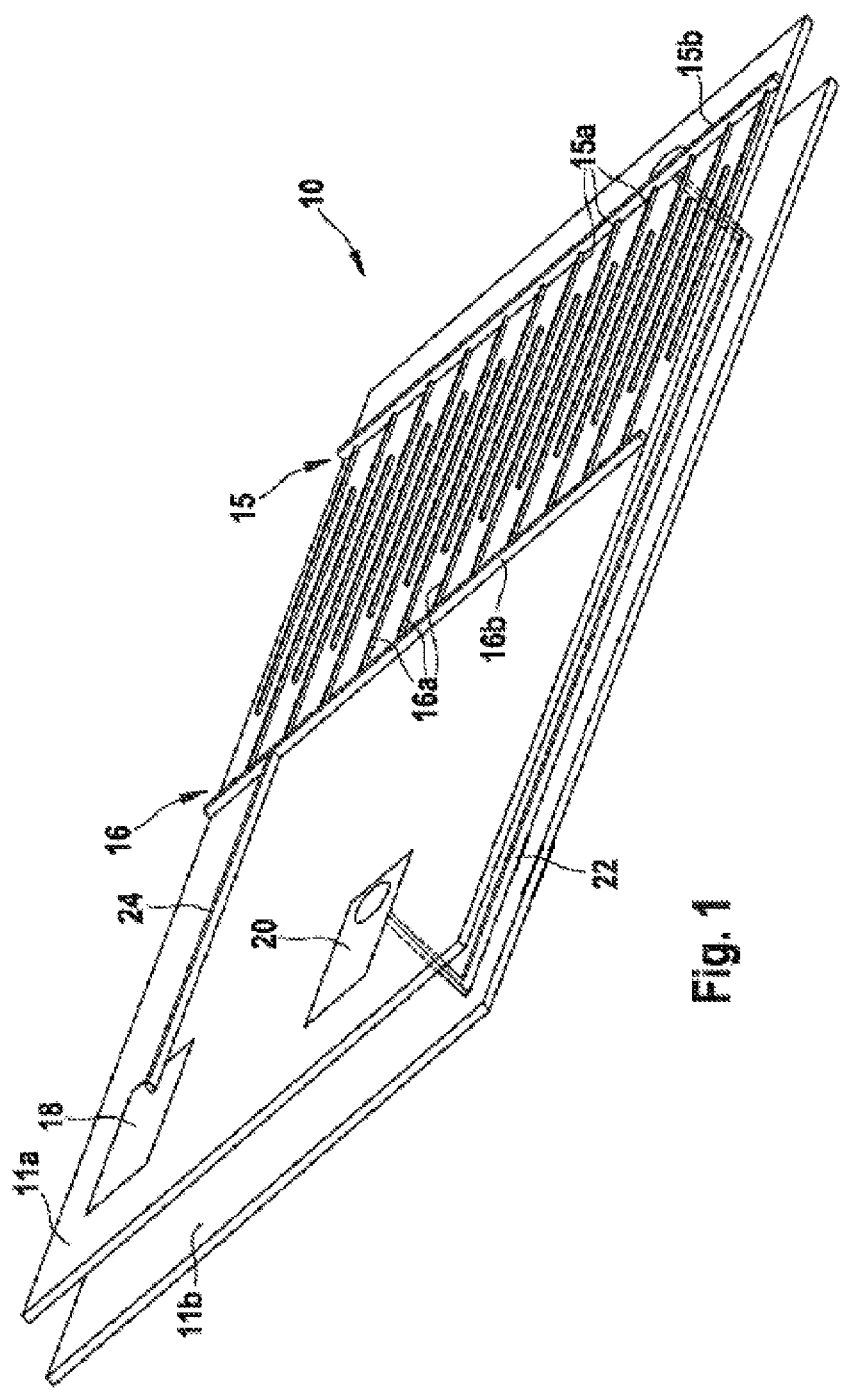
FIG. 1 shows a schematic representation of a sensor element for determining particles according to a first exemplary embodiment in an exploded representation.
Figure 2:
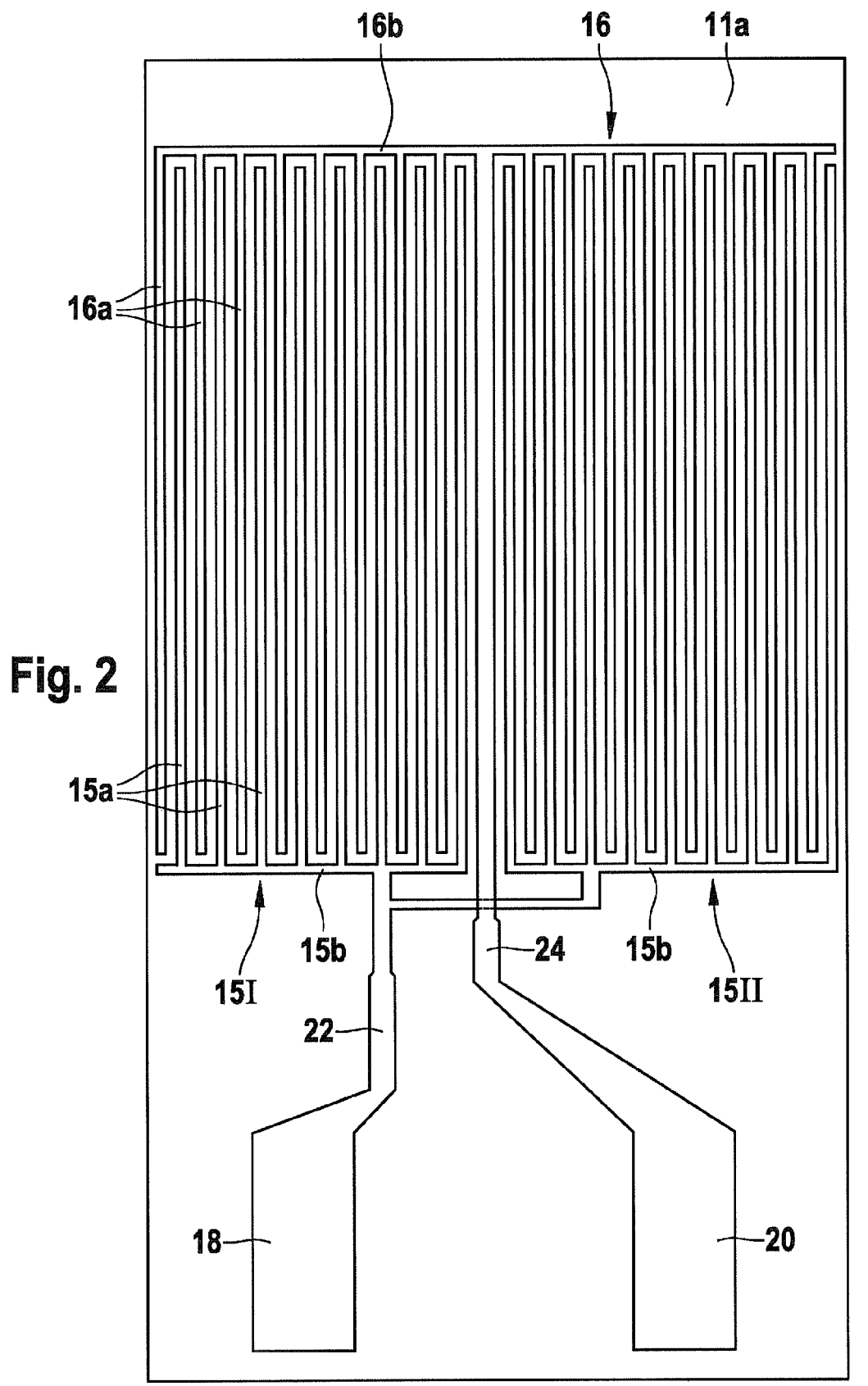
FIG. 2 shows the schematic representation of a sensor element for determining particles according to a second exemplary embodiment in a top view.

Unless noted otherwise, the reference numerals used in FIGS. 1 and 2 always refer to structural and system components having equivalent functions.

FIG. 1 shows a basic construction of a first specific embodiment of the present invention. A ceramic sensor element is designated by 10, and it is used for determining a particulate concentration, such as the soot concentration in a gas mixture surrounding the sensor element. Sensor element 10 includes a plurality of ceramic layers 11a and 11b, for example, which form a planar ceramic body. They are made up preferably of an electrically insulating material, such as aluminum oxide, barium-containing aluminum oxide or cerium dioxide. In one alternative specific embodiment, the ceramic layers are developed from an oxygen ion-conducting solid electrolyte material, such as $ZrO_2$ stabilized or partially stabilized with $Y_2O_3$, in this case all electrically conductive supply lines, for measuring electrodes or perhaps heating element or temperature sensor, being insulated from the surrounding solid electrolyte material by insulating layers (not shown), made of an electrically insulating ceramic material. A further possibility is using so-called low temperature cofired ceramics (LTCC) as the material of the ceramic layers.

The integrated form of the planar ceramic body of sensor element 10 is produced in a manner known per se, by laminating together the ceramic foils printed over with functional layers, and subsequently sintering the laminated structure.

On one large surface of the sensor element, for example, two measuring electrodes 15, 16 are applied, which are preferably developed as interdigital electrodes that are interleaved with each other. The use of interdigital electrodes as measuring electrodes 15, 16 allows an especially precise determination of the electrical resistance and the electrical conductivity of the surface material located between measuring electrodes 15, 16.

Contact surfaces 18, 20 are provided in the area of one end of the sensor element, facing away from the gas mixture, for contacting measuring electrodes 15, 16, and they are connected to measuring electrodes 15, 16 by electrode supply lines 22, 24.

During the operation of sensor element 10, a voltage is applied to measuring electrodes 15, 16. Since measuring electrodes 15, 16 are applied onto the surface of electrically insulating ceramic layer 11a, there is initially virtually no current flow between measuring electrodes 15, 16.

If a measuring gas flowing around sensor element 10 contains electrically conductive particles, soot, in particular, these will become adsorbed on the surface of ceramic layer 11a. If there is sufficient degree of saturation of the surface of ceramic layer 11a with soot, and since soot has a certain electrical conductivity, an increasing current flow will come about between measuring electrodes 15, 16, which correlates with the extent of the degree of saturation.

Now, if a preferably constant DC or AC voltage is applied to measuring electrodes 15, 16, and the current flow occurring between measuring electrodes 15, 16 is ascertained, an impedance change or a capacitance change is able to be recorded, and the degree of saturation of the sensor element with soot is able to be detected. Furthermore, from the integral of the current flow over time, one may draw a conclusion on the deposited particle mass or on the current particle mass flow, especially the soot mass flow, and the particle concentration in the gas mixture. Using this measuring method, the concentration is recorded of all those particles in a gas mixture which positively or negatively influence the electrical conductivity of the ceramic material located between measuring electrodes 15, 16.

The mounting of the electrode structures of measuring electrodes 15, 16 on ceramic layer 11a is able to take place directly by screen printing in cofire technology, or even subsequently to produce the ceramic base carrier by subsequent burning in of the structure by postfiring. The advantage of postfiring is in the additional usability of additional materials which would not endure sintering within the scope of cofiring at ca. 1400° C. Coating processes that function in a contactless manner, such as inkjet techniques, are available for applying measuring electrodes 15, 16.

Sensor element 10 also preferably has a ceramic heating element (not shown) which is developed as an electrical resistance conductor track and is used for heating up sensor element 10, particularly to the temperature of the gas mixture to be determined, and for the burning off of the soot particles deposited on the large surfaces of the sensor element. The resistance conductor track is preferably developed in the form of a meander. By applying an appropriate heating voltage to the resistance conductor track, the heating output of the heating element is able to be regulated appropriately.

Moreover, sensor element 10 may include a temperature sensor which is preferably developed in the form of an electrical resistance conductor track or, alternatively, as a thermocouple, NTC resistor or PTC resistor. The temperature sensor is used to measure the temperature of the gas mixture, and is used, among other things, to correct the temperature-dependent measured resistance of the ceramic material located between measuring electrodes 15, 16, and to correct for the diffusion deposit.

If the sensor element is used in a sensor for determining the soot concentration in an exhaust gas systems, and if, in this system, there exists a separate exhaust gas temperature sensor, or alternatively a control unit having a temperature model stored as a characteristics map, one may do without a temperature sensor integrated into the sensor element.

The production of sensor element 10 takes place in that, first of all, a plurality of ceramic sensor elements is produced on a common ceramic substrate, and these are then separated. Conditioned by production tolerances in the production of sensor elements, for instance, during the application of measuring electrodes 15, 16 using screen printing, only a limited range of the sensor surface is available, in the usual sensor elements, since when exceeding this range, there is the danger that the conductive paths of the measuring electrodes are damaged in the subsequent separation of the sensor elements, and there will be a total failure of the sensor element.

By contrast, the positioning of measuring electrodes 15, 16 and electrode supply lines 22 or 24 in a sensor element according to the present invention takes place in such a way that, when severing the conductive paths of one of measuring electrodes 15, 16, there is no impairment of the functionality of measuring electrodes 15, 16. Measuring electrodes 15, 16 are preferably developed as interdigital electrodes, the interdigital electrodes having a row of intermeshing branches 15a, 16a, as well as each having a main line 15b, 16 b by which branches 15a, 16a are connected in an electrically conductive manner; and the branches of interdigital electrodes 15a, 16a being aligned essentially in parallel to a longitudinal axis of sensor element 10. Main conductors 15b, 16b, in this context, are preferably placed at an outer edge, that is perpendicular to a longitudinal axis of sensor element 10, of ceramic layer 11a, and are consequently positioned over the entire width of sensor element 10, so that they are severed during the separation of sensor element 10. However, in this context, there is no failure in the respective measuring electrode as in the usual sensor elements, but only individual branches are cut off. This yields minimal differences in the sensor elements with respect to their measuring electrodes 15, 16, which differ by at most one branch 15a, 16a, whereby the size of the sensitive range may deviate by the distance between two branches 15a, 16a, which is able to amount to 40 to 200 µm, especially 60 to 170 µm.

The special advantage of this electrode positioning is that the sensitive range of sensor element 10, formed by intermeshing measuring electrodes 15, 16, is maximized, and that the sensitive range is broadened particularly also in the vicinity of the outer edges of ceramic layer 11a, which is of great importance for the sensitivity of sensor element 10.

In order to implement this electrode positioning, preferably at least one of electrode supply lines 22 or 24 is run in a different layer plane of sensor element 10, for example, in the layer plane of ceramic layer 11b. The contacting of electrode supply line 22, that is guided in a different layer plane of ceramic sensor element 10, takes place using through-hole plating, in order to ensure the electrical connection of electrode supply lines 22 to contact location 20 and measuring electrode 15.

Furthermore, electrode supply lines 22 or 24 are preferably applied on ceramic layer 11a, 11b, using a safety distance from the outer edges of sensor element 10, since, when they are severed, the appertaining measuring electrode 15, 16 would become no longer functional. In this way, branches 15a, 16a have, at least in some ranges, a greater distance from a longitudinal symmetrical axis of sensor element 10 than electrode supply lines 22 or 24.

An additional specific embodiment of the present invention is shown in FIG. 2. One of the two measuring electrodes 15, 16 is developed in the form of two partial electrodes 15I, 15II, in this context. The two partial electrodes 15I, 15II have a common electrode supply line 22 which branches, for example, in the vicinity of measuring electrode 15, each partial electrodes 15I, 15II being contacted by a branch. The two partial electrodes 15I, 15II, in this context, are positioned on the surface of ceramic layer 11a in such a way that, particularly in the middle between the partial electrodes 15I, 15II, electrode supply line 24 of second measuring electrode 16 is able to be placed without coming into an electrical contact with one of the two partial electrodes 15I, 15II. However, since electrode supply lines 22, 24 cross in this arrangement of measuring electrodes 15, 16, the two electrode supply lines 22, 24 are run in different layer planes of sensor element 10 in the areas where they cross, or at least are mounted separately from each other by using an insulating ceramic layer. One alternative design approach provides that each of partial electrodes 15I, 15II have a separate electrode supply line, and consequently, three contact locations are provided for contacting measuring electrodes 15I, 15II, 16.

The sensor element according to the present invention is particularly suitable for determining the soot concentration in the exhaust gases of internal combustion engines or of stationary combustion systems such as heating plants, turbines or power stations. It is, however, also suitable for determining the particulate concentration in fluids that are used, for instance, in the chemical industry.

What is claimed is:

1. A sensor element for determining a gas component or particles in a measuring gas, comprising:
    a first measuring electrode and a second measuring electrode, the measuring electrodes being interdigital electrodes, each of the interdigital electrodes having a row of intermeshing branches, and a main line to which the branches are connected in an electrically conducting manner, the main line extending over an entire width of the sensor element, the branches of the interdigital electrodes being aligned in parallel to a longitudinal axis of the sensor element; and
    an electrode supply line for each of the first measuring electrode and the second measuring electrode, wherein the electrode supply line of the first measuring electrode is run at least primarily in a different ceramic layer plane than the electrode supply line of the second measuring electrode.

2. The sensor element as recited in claim 1, wherein a distance apart of two adjacent branches of the same measuring electrode amounts to between 40 and 200 μm.

3. The sensor element as recited in claim 1, further comprising:
    one of a heating element or a temperature sensor integrated into the sensor element.

4. A method for producing the sensor element of claim 1, comprising:
    producing at least two sensor elements on a common substrate, and subsequently separating them; wherein at least one of the electrodes of the sensor element is severed during the separation, wherein the at least one electrode is an interdigital electrode having a row of intermeshing branches and a main line which is connected to the branches in an electrically conducting manner, and at least one of the main lines is severed during the separation.

5. The sensor element as recited in claim 1 wherein the sensor element is for determining soot in exhaust gases of one of an internal combustion engine or a stationary combustion installation.

6. A sensor element for determining a gas component or particles in a measuring gas, comprising:
    a first measuring electrode and a second measuring electrode on a ceramic body of the sensor element, the measuring electrodes being interdigital electrodes, each of the interdigital electrodes having a row of intermeshing branches, and a main line to which the branches are connected in an electrically conducting manner, the branches of the interdigital electrodes being aligned in parallel to a longitudinal axis of the sensor element, wherein the branches of at least one interdigital electrode being positioned at a greater distance from a longitudinally symmetrical axis of the sensor element than electrode supply lines of the interdigital electrodes, since at least one of the measuring electrodes is guided to an outer edge of the sensor element, wherein the electrode supply line of the first measuring electrode is run at least primarily in a different ceramic layer plane than the electrode supply line of the second measuring electrode.

7. The sensor element as recited in claim 6, wherein a distance apart of two adjacent branches of the same measuring electrode amounts to between 40 and 200 μm.

8. The sensor element as recited in claim 6, further comprising:
    one of a heating element or a temperature sensor integrated into the sensor element.

9. The sensor element as recited in claim 6 wherein the at least one of the measuring electrodes is positioned the outer edge of the sensor element.

10. The sensor element as recited in claim 6 wherein the main line is positioned at an outer edge of the sensor element.

11. The sensor element as recited in claim 6 wherein the outer edge is perpendicular to a longitudinal axis of the sensor element.

12. The sensor element as recited in claim 6 wherein contact surfaces are provided at a second outer edge of the sensor element.

13. The sensor element as recited in claim 6 wherein one of the measuring electrodes is formed from two half electrodes which are connected to each other, in an electrically conducting manner, only via one electrode supply line.

* * * * *

UNITED STATES PATENT AND TRADEMARK OFFICE
CERTIFICATE OF CORRECTION

PATENT NO. : 8,402,813 B2  Page 1 of 1
APPLICATION NO. : 12/530395
DATED : March 26, 2013
INVENTOR(S) : Kruse et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 266 days.

Signed and Sealed this
First Day of September, 2015

Michelle K. Lee
*Director of the United States Patent and Trademark Office*